(12) United States Patent
Farina et al.

(10) Patent No.: US 9,125,898 B2
(45) Date of Patent: Sep. 8, 2015

(54) ACETAM DERIVATIVES FOR PAIN RELIEF

(75) Inventors: Carlo Farina, Valsoda (IT); Carla Ghelardini, Candeglia (IT); Ruggero Fariello, Lugano (CH)

(73) Assignee: NEUROTUNE AG, Schlieren (CH)

( * ) Notice: Subject to any disclaimer, the term of this patent is extended or adjusted under 35 U.S.C. 154(b) by 857 days.

(21) Appl. No.: 12/566,055

(22) Filed: Sep. 24, 2009

(65) Prior Publication Data

US 2010/0125096 A1 May 20, 2010

Related U.S. Application Data

(60) Provisional application No. 61/114,835, filed on Nov. 14, 2008.

(51) Int. Cl.
*A61K 31/4188* (2006.01)
*A61K 31/40* (2006.01)

(52) U.S. Cl.
CPC ............ *A61K 31/40* (2013.01); *A61K 31/4188* (2013.01)

(58) Field of Classification Search
USPC ................................. 514/393, 424
See application file for complete search history.

(56) References Cited

U.S. PATENT DOCUMENTS

2007/0244143 A1* 10/2007 Barlow et al. ............... 514/282
2010/0286188 A1* 11/2010 Bachurin et al. ............ 514/292

FOREIGN PATENT DOCUMENTS

| WO | WO-2004/085438 | 10/2004 |
|---|---|---|
| WO | WO-2008/058988 | 5/2008 |
| WO | WO-2008/125674 | 10/2008 |
| WO | WO-2009/103176 | 8/2009 |

OTHER PUBLICATIONS

Andreason et al., "A Comparative Pharmacokinetic Study in Healthy Volunteers of the effect of Carbamazepine and Oxcarbazepine on Cyp3a4", *Epilepsia* 48(3):490-496, 2007.

Ballantyne et al., "Efficacy of Opioids for Chronic Pain," *Clin J Pain* 24(6):469-78, Jul./Aug. 2008.
Barcs et al., "Effectiveness and tolerance of clobazam in temporal lobe epilepsy." *Acta Neurol Scand* 93: 88-93, 1996.
Culberson et al., "Prescription drug misuse/abuse in the elderly," *Geriatrics* 63(9): 22-31, Sep. 2008.
Dray, A., "Neuropathic pain: emerging treatments," *Br J Anaesth* 101 (1):48-58, 2008.
Farina et al., "Synthesis and biological evaluation of novel dimiracetam derivatives useful for the treatment of neuropathic pain," *J Bioorg. Med. Chem.* 2008 doi:10.1016/j.bme.2007.12.015.
Fernihough et al., "Pain related behaviour in two models of osteoarthritis in the rat knee," *Pain* 112: 83-93, 2004.
Giurgea et al., "Differential Pharmacological Reactivity of Three Types of Cortical Evoked Potentials", *Arch. Int. Pharmocodyn* 188: 401-404, 1970.
Guingamp et al., "Mono-Iodoacetate-Induced Experimental Osteoarthritis," *Arthritis Rheum* 40(9): 1670-1679, Sep. 1997.
Gupta et al., "Tolerance and Withdrawal to Anticonvulsant Action of Clonazepam: Role of Nitric Oxide", *Methods Find Exp Clin Pharmacol*, 22(4): 229-235, 2000.
Jensen et al., "Management of neuropathic pain," *Curr Opin Support Palliat Care*, 1:126-131, 2007.
Licata et al., "Abuse and Dependence Liability of Benzodiazepine-Type Drugs: $GABA_A$ Receptor Modulation and Beyond", *Pharmacol Biochem Behav*, 90:74-89, 2008.
McConnell, JG, "Benzodiazepine tolerance, dependency, and withdrawal syndromes and interactions with fluoroquinolone antimicrobials," *Br J Gen Pract* 58(550):365-366 (2008).
Perucca, E., "Clinically relevant drug interactions with antiepileptic drugs", *Br J Clin Pharmacol* 61(3):246-255 (2006).
Pinza et al., "Synthesis and Pharmacological Activity of a Series of Dihydro-1H-pyrrolo[1,2-a]imidazole-2,5(3H,6H)-diones a Novel Class of Potent Cognition Enhancers", *J Med Chem* 36: 4214-4222, 1993.
Zanotti et al., "Abecarnil enhances recovery from diazepam tolerance," *Neuropharmacology* 38: 1281-1288, 1999.

\* cited by examiner

*Primary Examiner* — Shirley V Gembeh
(74) *Attorney, Agent, or Firm* — Marshall, Gerstein & Borun LLP

(57) ABSTRACT

The present invention provides a method of treatment, prevention and/or delay of progression of neuropathic pain by a specific dosing regime of acetam derivatives.

10 Claims, 3 Drawing Sheets

ACETAM DERIVATIVES FOR PAIN RELIEF

TECHNICAL FIELD

This invention relates to the use of compositions comprising acetam derivates for pain relief.

BACKGROUND ART

Today's treatment of chronic pain conditions rests mostly on the use of FANS, anaesthetics, opioids, antiepileptic drugs, and antidepressants (Jensen T S, Finnerup N B: Management of neuropathic pain. Curr Opin Support Palliat Care. 2007 August; 1(2):126-31; Dray A. Neuropathic pain: emerging treatments. Br J Anaesth. 2008 July; 101(1):48-58). Each one of these classes of drugs has serious drawbacks to the point that in the pharmacological industry the field is considered as a high unmet medical need. Incomplete efficacy, development of tolerance and addiction, serious side effects are all unwanted results of the present therapeutic regimes for the various forms of pain, particularly the one classified as of neuropathic nature.

Neuropathic pain (NP) is defined as the one caused by direct dysfunction of the nervous system (Jensen T S, Finnerup N B: Management of neuropathic pain. Curr Opin Support Palliat Care. 2007 August; 1(2):126-31; Dray A. Neuropathic pain: emerging treatments. Br J Anaesth. 2008 July; 101(1):48-58), as opposed to the inflammatory pain that is due to release of algogens by surrounding tissues. The inflammatory pain serves the function of calling the body's attention to the injured part, whereas NP does not serve any beneficial purpose. Through wind up mechanisms, NP has the tendency to ingravescence and become chronic. Of course, in clinical practice it is very common to see mixture of inflammatory and neuropathic forms of pain as prototypically illustrated by osteoarthritic patients.

Addiction (or dependency) may cause serious medical conditions when treatment is interrupted (Culberson J W, Ziska M. Prescription drug misuse/abuse in the elderly. Geriatrics. 2008; 63:22-31; Licata S C, Rowlett J K. Abuse and dependence liability of benzodiazepine-type drugs: GABA (A) receptor modulation and beyond. Pharmacol Biochem Behav. 2008; 90:74-89; Oulis P, Masdrakis V G, Karakatsanis N A, Karapoulios E, Kouzoupis A V, Konstantakopoulos G, Soldatos C R. Pregabalin in the discontinuation of long-term benzodiazepine use: a case-series. Int Clin Psychopharmacol. 2008; 23:110-2; McConnell J G. Benzodiazepine tolerance, dependency, and withdrawal syndromes and interactions with fluoroquinolone antimicrobials. Br J Gen Pract. 2008; 58:365-6; Ballantyne J C, Shin N S. Efficacy of opioids for chronic pain: a review of the evidence. Clin J Pain. 2008; 24:469-78).

Effectiveness of chronic pharmacological treatment in neuropsychiatric and chronic pain conditions is often hampered by the development of tolerance (McConnell J G. Benzodiazepine tolerance, dependency, and withdrawal syndromes and interactions with fluoroquinolone antimicrobials. Br J Gen Pract. 2008; 58:365-6; Zanotti A, Natolino F, Contarino A, Lipartiti M, Giusti P. Abecarnil enhances recovery from diazepam tolerance. Neuropharmacology. 1999; 38:1281-8; Gupta N, Bhargava V K, Pandhi P. Tolerance and withdrawal to anticonvulsant action of clonazepam: role of nitric oxide. Methods Find Exp Clin Pharmacol. 2000; 22:229-35; Barcs G, Halász P. Effectiveness and tolerance of clobazam in temporal lobe epilepsy. Acta Neurol Scand. 1996; 93:88-93) manifested by loss of efficacy that may be partly, but not always, compensated by an increased daily dose. This compensatory manoeuvre entails the risk of increased unwanted side effects eventually resulting in diminished compliance or abandonment of the treatment (Jensen, T S; Finnerup, N B: Management of neuropathic pain. Curr Opin Support Palliat Care (2007), 1(2): 126-31; Ballantyne J C, Shin N S: Efficacy of opioids for chronic pain: a review of the evidence. Clin J Pain (2008) 24:469-78).

Other drugs (notably, but not only antiepileptic drugs [AEDs]) and some anti depressant agents may induce their own metabolism, yet another cause of lower serum levels, shorter half life in the patients body and diminished efficacy (Andreasen A H, Brøsen K, Damkier P. A comparative pharmacokinetic study in healthy volunteers of the effect of carbamazepine and oxcarbazepine—on cyp3a4. Epilepsia. 2007, 48:4906; Perucca E. Clinically relevant drug interactions with antiepileptic drugs. Br J Clin Pharmacol. 2006; 61:246-55.).

In view of the above, it is evident that there is a need in the art to reduce the problems of the present therapeutic regimes.

DISCLOSURE OF THE INVENTION

It was surprisingly found that a specific dosing regime with acetam derivatives results in both an enhanced efficacy and a prolonged therapeutic action. Specifically, the dose per administration is diminished and/or the administration schedule more spaced in time (i.e. once a day versus twice a day (b.i.d.) or several times per day).

Hence, it is a general object of the invention to provide a method of treatment, prevention, and/or delay of progression of pain with a dosing regime of an acetam derivative.

Now, in order to implement this and still further objects of the invention, which will become more readily apparent as the description proceeds, the dosing regime is manifested by the features that in a first phase an initial therapeutically effective dose of an acetam derivative is administered twice daily or more often in subdoses to a subject in need thereof and subsequently, in a second phase, a lower dose of said acetam derivative is administered to said subject and/or said dose is administered more spaced in time, i.e. once a day (u.i.d.) or at an even longer interdose interval such as e.g. once every other day. The amount of the initial dose is 0.25-4 g per diem (day) of said acetam derivative; furthermore, the amount of the initial dose is at least 1.5-4 times, more preferably at least 2 times, the total average daily dose of said acetam derivative in the subsequent dose. The initial dose is administered for at least 7 days.

The administration schedule described herein has the advantage that acetam derivatives which once have produced a beneficial effect in the subject can maintain said effect by administration of lower daily doses, e.g. by administering lower amounts and/or with a change in schedule from two, three, four times a day to once a day or even more spaced administrations, e.g. every other day or every third day.

A further advantage consists in the possibility to maintain the pain relief achieved by the administration of anti neuropathic pain agents (including but not limited to gabapentin, pregabalin, duloxetine, opioid derivatives, antiepileptic agents such as tegretol, topiramate, phenyloin, valproic acid, lamotrigine etc) with acetam derivatives, specifically, but not limited to dimiracetam, NT-11624, NT-13317, NT-11336, NT-11337, piracetam, aniracetam, oxiracetam, nefiracetam, levetiracetam, brivaracetam, seletracetam, rolziracetam, NT-15019, NT-24336, NT-24337.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

Figure 1:
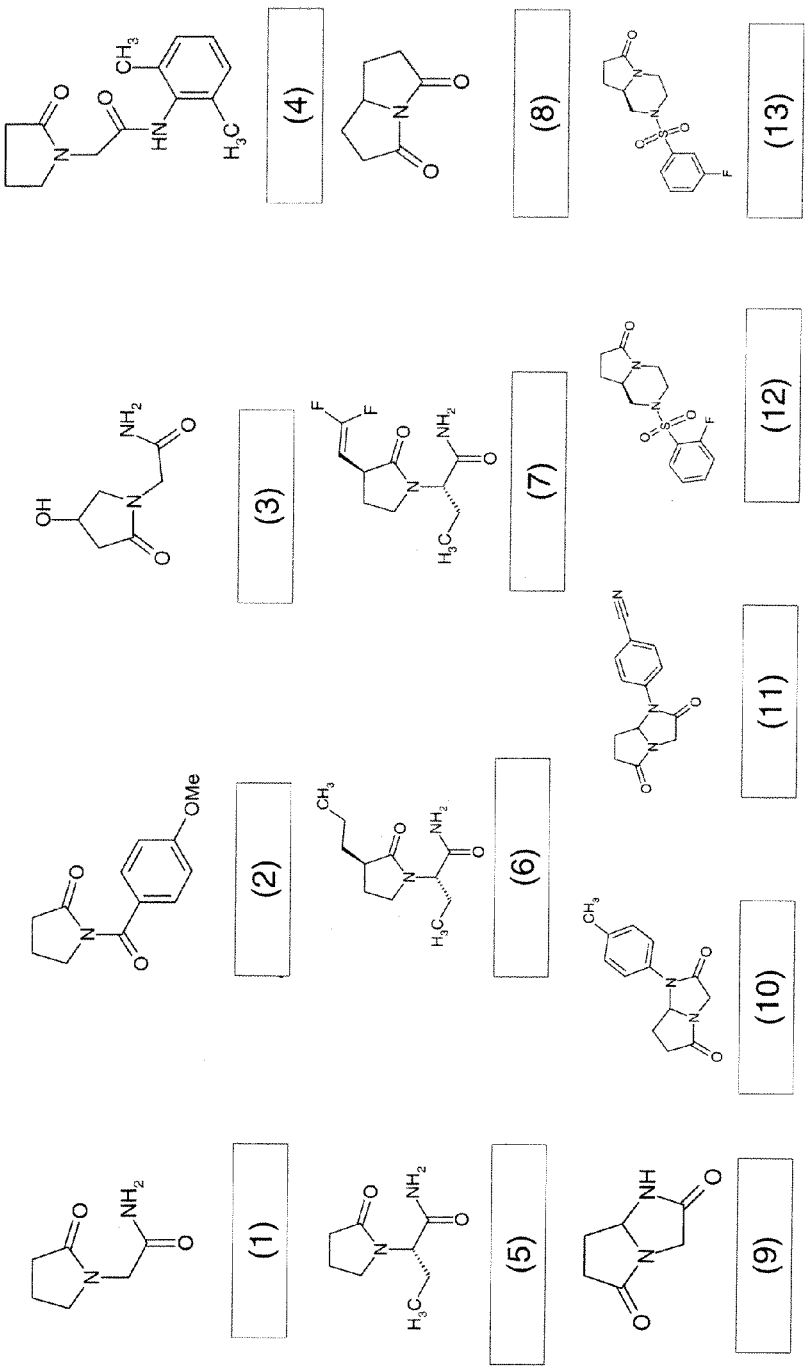
FIG. 1 shows an overview of some exemplary acetam derivatives. Formula No. 1: piracetam; formula No. 2: aniracetam; formula No. 3: oxiracetam; formula No. 4: nefiracetam; formula No. 5: levetiracetam; formula No. 6: brivaracetam; formula No. 7: seletracetam; formula No. 8: rolziracetam; formula No. 9: dimiracetam; formula No. 10: NT-13317; formula No. 11: NT-15019; formula No. 12: NT-24336; formula No. 13: NT-24337.

In a first aspect, the invention provides a method of treatment, prevention and/or delay of progression of neuropathic pain comprising the steps of administering to a subject in need thereof
(a) in a first phase an initial therapeutically effective dose of an acetam derivative divided in at least two subdoses; and
(b) subsequently administering in a second phase a lower average daily dose of said acetam derivative to said subject and/or at longer interdose interval such as once a day (u.i.d.) or once every other day.

The amount of the initial dose is at least 1.5-4 times, more preferably at least 2 times, the total average daily amount of said acetam derivative in the subsequent dose and the initial dose is administered for at least 7 days.

Within the context of the present invention, the term "acetam derivatives" refers to a class of nootropic drugs that share a 2-pyrrolidinone nucleus and derivatives thereof.

Within the context of the present invention, the terms (average) daily dosage and (average) daily dose are used interchangeably, while a dosage unit designates a dosed unit for administration, e.g. a tablet. Dependent on the context, one or more dosage units may make up for one dose or one subdose.

The first acetam is piracetam (formula 1), a cyclic relative of GABA (γ-aminobutyric acid) that has been in clinical use for more than 40 years used in the treatment of alcoholism, dementia, stroke, epilepsy, parkinsonism, schizophrenia, AD and dyslexia (Giurgea, C.; Moyersoons, F. Arch. Int. Pharmacodyn. Ther., 1970, 188, 401). Piracetam was the prototype for the development of other pyrrolidinone nootropics. The original structure of piracetam has undergone considerable modifications, albeit most compounds have maintained the 2-oxopyrrolidine ring. This ring has been successfully substituted in almost every position, and also condensed with other rings, as in dimiracetam (formula 9) (Pinza, M.; Farina, C.; Cerri, A.; Pfeiffer, U.; Riccaboni, M. T.; Banfi, S.; Biagetti, R.; Pozzi, O.; Magnani, M.; Dorigotti, L. J. Med. Chem., 1993, 36, 4214) or in rolziracetam (8) in which the 5,5-bicyclic system was reported to be optimal for activity against ECS induced amnesia (Butler, D. E., U.S. Pat. No. 4,638,006 of Jan. 20, 1987). Novel derivatives of levetiracetam (formula 5), such as brivaracetam (formula 6) and seletracetam (formula 7); dimiracetam (formula 9), its derivatives NT-13317 and NT-15019 (formula 10 and 11, respectively), and novel 1,4-diazabicyclo[4.3.0]nonan-9-ones (NT-24336 and NT-24337, see formulas 12 and 13, respectively). In particular, the pyrroloimidazole derivatives as disclosed in WO04/085438 (the teachings of which are herein included by reference), such as NT-13317 (1-p-tolyl-tetrahydropyrrolo[1,2a] imidazole-2,5-dione, see formula 10; described in WO08/058,988, also included by reference) are understood as being acetam derivatives.

The acetam derivative of the method disclosed herein may be any acetam derivative; preferably, the acetam derivative is selected from the group consisting of piracetam, oxiracetam, aniracetam, nefiracetam, rolziracetam, levetiracetam or derivatives thereof (such as brivaracetam or seletracetam), NT-24336, NT-24337, dimiracetam or derivatives thereof (e.g. NT-13317 or NT-15019). In a much preferred embodiment, the acetam derivative is dimiracetam, (2,5-dioxo-hexahydro-1H-pyrrolo[1,2-a]imidazole, see formula 9). Dimiracetam is also known in the art as NT-11624.

Preferably, the amount of the initial dose is 0.25-4 g per day of said acetam derivative. As mentioned above, said daily dose may be administered in an initial phase in several subdoses or divided doses that together make up for the daily dose. Such administration in subdoses or divided doses may e.g. be twice or three times a day (b.i.d. or t.i.d., respectively). In a subsequent second phase, said daily dose is lowered and/or administered more spaced in time, e.g. once a day or even less (e.g. once every other day or once every third day) resulting in an average daily dose that is lower than the overall daily dosage administered during the first phase.

Within the scope of the present invention, by the term "administered" it is meant that the acetam derivative is delivered to a subject by any means or route which is effective to achieve the desired result, including oral, parenteral, enteral, intraperitoneal, topical, transdermal (e.g. using any standard patch), subcutaneous, intravenous, intramuscular, buccal, sublingual, rectal, vaginal, intra-arterial, intrathecal administration.

The acetam derivatives may be pharmaceutically formulated according to known methodologies. The various pharmaceutical compositions may be selected according to the needs of the treatment. They may be formulated e.g. as fast release formulation or as sustained release formulation or as combination thereof.

Such compositions can be prepared by mixing and can be suitably adapted for oral or parenteral administration, and as such, can be administered e.g. in the form of tablets, capsules such as gelatine capsules, oral preparations, powders, granules, pellets, liquid solutions for injection or infusion, suspensions or suppositories.

Tablets and capsules for oral administration are usually supplied in dosage units and may contain conventional excipients such as binders, fillers, diluents, tabletting agents, lubricants, detergents, disintegrants, colorants, flavors and wetting agents. Tablets may be coated in accordance to methods well known in the art.

Suitable fillers include for example cellulose, mannitol, lactose and similar agents. Suitable disintegrants include starch, polyvinylpyrrolidone and starch derivatives such as sodium starch glycolate. Suitable lubricants include, for example, magnesium stearate. Suitable wetting agents include for example sodium lauryl sulfate.

These solid oral compositions can be prepared with conventional mixing, filling or tabletting methods. The mixing operations can be repeated to disperse the active agent in compositions containing large quantities of fillers. These operations are conventional.

The oral liquid compositions can be provided in the form of, for example, aqueous or oily suspensions, solutions, emulsions, syrups or elixirs or in the form of a dry product to be reconstituted with water or with a suitable liquid carrier at the time of use. The liquid compositions can contain conventional additives such as suspending agents, for example sorbitol, syrup, methylcellulose, gelatin, hydroxyethylcellulose, carboxymethylcellulose, aluminium stearate gel or hydrogenated edible fats, emulsifying agents, for example lecithin, sorbitan monooleate, or acacia; non aqueous carriers (which can include edible oil) for example almond oil, fractionated coconut oil, oily esters such as glycerin esters, propylene glycol or ethyl alcohol; preservatives, for example methyl or propyl p-hydroxybenzoate or sorbic acid and if desired, conventional flavours or colorants.

Oral formulations also include conventional sustained release formulations, such as tablets or granules with enteric coating.

For parenteral administration, fluid dosage units can be prepared containing the active compounds and a sterile carrier. The active compounds, depending on the carrier and concentration, can be suspended or dissolved. The parenteral solutions are normally prepared by dissolving the compound in a carrier and sterilizing by filtration, before filling suitable vials or ampoules and sealing. Adjuvants such as local anaesthetics, preservatives and buffering agents can be advantageously dissolved in the carrier. In order to increase stability, the composition can be frozen after filling the vial and the water removed under vacuum. The parenteral suspensions are prepared essentially in the same way, with the difference that the active compounds can be suspended rather than dissolved in the carrier, and can be sterilized by exposure to ethylene oxide prior to being suspended in the sterile carrier. A surfactant or humectant can be advantageously included to facilitate uniform distribution of the compound of the invention.

A further method of administration for the compound of the invention refers to a topic treatment. Topic formulations may contain for example ointments, creams, lotions, gels, solutions, pastes and/or may contain liposomes, micelles and/or microspheres.

A further method of administration for the compounds of the invention is transdermal delivery. Typical transdermal formulations include conventional aqueous and non-aqueous carriers, such as creams, oil, lotions or pastes or may be in the form of membranes or medicated patches.

As is the common practice, the compositions are normally accompanied by written or printed instructions, for use in the treatment concerned.

Compositions may be administered at any suitable time. For example, compositions can be administered before, after or together with an activity, e.g. prior to, during or after a meal.

An "effective amount" relates to the indication that the compositions and methods are useful to encourage, elicit, cause and/or produce the biochemical and/or physiological effects indicated above. The invention is not limited by how much blood/serum parameters are promoted or facilitated. Other parameters influencing the "effective amount" include diet, exercise and hereditary factors.

The initial therapeutically effective dose may be determined e.g. in clinical trials or empirically, e.g. based on clinical experience and/or clinical experience with other acetam drugs. For example, the recommended daily dosage of piracetam usually ranges from 1.6-9.6 grams daily (2-12 pills daily as piracetam is usually supplied in 800 mg tablets or capsules). Faster therapeutically efficacy was reported when taking 1-2 pills every hour for 4-6 hours or taking 4-8 pills at once for the first few days. Aniracetam is commonly used in daily doses of 750-3,000 mg which are usually administered in 2-3 subdoses. Levetiracetam is typically administered in a dose of 750-3500 mg per day.

When a therapeutic effect has been achieved during the first phase, usually after at least 7 days, typically after 7 to 14 days, or 7 up to 28 days, the treatment modality may be changed to the second, subsequent phase with lower dose. Such lower dose may be achieved in that the daily dose of the acetam derivative is diminished while keeping the schedule of the administration of the diminished, i.e. lower doses constant and/or in that the schedule of administration is changed from several times a day to once a day or to administrations even more spaced in time. If the schedule of administration is changed to less frequent administration or longer interdose interval, respectively, the dosage of each administration is chosen such that the average daily dosage in phase two is lower than the daily dosage in phase one.

The average daily dose in phase two is calculated on the basis of the time interval between two subsequent administrations. Therefore, if the compound is administered every other day, the average daily dosage will correspond to one half of the dose, or if the compound is administered every third day the average daily dosage will correspond to one third of the dose.

Whereas the dose in phase one is linked to the drug half life (in humans e.g. 7 h with a consequent high preference or even need of b.i.d. administration) in phase two dosing can be spaced down to once a day or even more spaced, such as e.g. up to once every second or third or fourth day, i.e. greater than 15 times the product half life, as shown in the experiments unveiled in this application.

The subject to whom the acetam derivative is administered is preferably a mammal, more preferably a human being.

By means of the claimed method it is possible to treat effectively and with high safety all kinds of chronic pain, either neuropathic or inflammatory in origin. Preferred examples of chronic pain treated according to the present invention are the following:

1. pain induced by chemotherapeutic agents or other antiblastic therapy (e.g. radiotherapy); exemplary chemotherapeutic agents responsible for neuropathies are taxol, vincristine, cisplatin, and oxaliplatin.

2. pain induced by antiviral agents such as nucleoside reverse transcriptase inhibitors (e.g. ddC, d4T, AZT);

3. complex regional pain syndrome, phantom limb, thalamic syndromes, spinal syndromes;

4. pain induced by osteoarthritis, rheumatoid arthritis, autoimmune osteoarthrosis forms;

5. pain induced by cephalea (cephalea in general and hemicranic forms; cephalea due to vascular, infective, autoimmune, dysmetabolic and tumoral causes, cephalea from endocranial hypertension, cephalea from pseudotumor cerebri, classic hemicrania with and without aura, hemiplegic hemicrania and with other motor complications, childhood and juvenile hemicrania, Bickerstaff's syndrome, etc.).

6. pain induced by fibromyalgia.

Of outstanding efficacy, and therefore preferred in the scope of the invention, is the treatment of pain induced by antiviral agents, chemoterapic agents, osteoarthritis, rheumatoid arthritis and autoimmune osteoarthritis.

In a preferred embodiment of the invention, the neuropathic pain is pain induced by antiviral and chemoterapic agents in patients infected by retroviruses and the acetam derivative is dimiracetam. In said case, the initial amount of dimiracetam is preferably 0.8 to 6 g per day administered in 2 or 3 divided doses. This daily dose and administration frequency is preferably applied for 7-14 days or for 7 up to 28 days. The subsequent dose is preferably 0.2 g-2 g administered once a day or at longer interdose interval, e.g. every other day.

In another preferred embodiment of the invention, the neuropathic pain is caused by osteoarthritis and the acetam derivative is dimiracetam. In said case, the initial amount of dimiracetam is 0.8 to 6 g per day administered in two or three divided doses. The initial dose is preferably administered for 7-14 days or for 7 up to 28 days and the subsequent dose is 0.2 g-2 g administered once a day or at longer interdose interval, e.g. every other day.

In a second aspect, the invention provides a pharmaceutical administration form containing a plurality of dosage units wherein said dosage units for the first and the second phase of the treatment as described above are physically separated. Preferably, the dosage units for said first phase each contains 0.2-6 g (preferred 0.2 to 3 g for administration twice a day) of said acetam derivative and the dosage units for said first phase each contains at least 1.5 times, more preferably at least 2 times, the amount of one dosage unit for said second phase.

In a preferred embodiment, said pharmaceutical administration form comprises at least 14 dosage units composed for said first phase arranged for bi-daily administration (i.e. two dosage units per day or one per administration), preferably 14 to 28 dosage units composed and arranged for bi-daily administration (i.e. such administration form comprising 28 dosage units is suitable for either 14 days administration of one unit twice a day or 7 day administration of two units twice a day).

Preferably, the dosage units are arranged sequentially within the pharmaceutical administration form.

Preferably, the dosage units for the first and for the second phase are labeled, more preferably, they are individually labeled.

Figure 5:
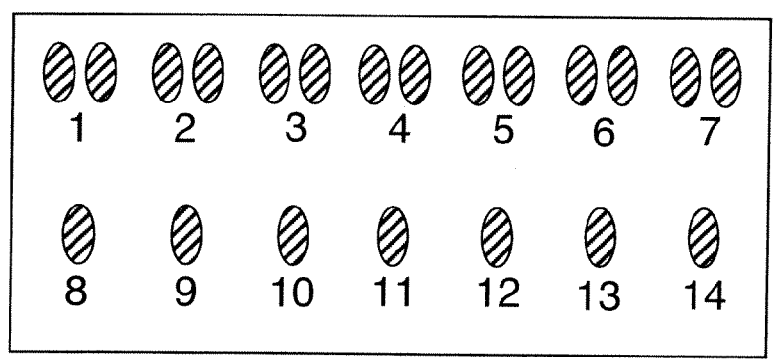
FIG. 5 shows one embodiment of a blister, e.g. for a 7 day administration of a first phase dosage twice a day and a 7 day administration of a second phase dosage once a day.

In a preferred embodiment, the pharmaceutical administration form is a blister pack. One embodiments for a blister for initial 7 day administration twice a day and a subsequent 7 day administration once a day is shown in FIG. 5 that also indicates the day of treatment for enhancing security. As an alternative to the indication of the day of treatment, the day of the week might be indicated. In an alternative embodiment, the doses for the first phase and the second phase are on separate blisters. Such blisters, e.g. one for the first and one for the second stage may e.g. be packed together for initial use or they may be packed in different packages. If longer treatment is envisaged, further second phase blisters might be offered in separate packages.

The acetam derivative is preferably selected from the group consisting of piracetam, oxiracetam, levetiracetam or derivatives thereof (e.g. brivaracetam or seletracetam), dimiracetam or derivatives thereof (e.g. NT-13317 or NT-15019), NT-24336 and NT-24337, most preferably dimiracetam.

EXPERIMENTAL DATA

A series of experiments confirmed that administration of NT-13317 or NT-11624 in animal models of neuropathic pain induced by loose ligation of the sciatic nerve or systemic administration of chemotherapy, antiviral, diabetic causing molecules as well as in a model of knee osteoarthritis (OA) was not inducing tolerance, but on the contrary showed an incremental response. For example, after having induced in rats a polyneuropathy with the anticancer agent oxaliplatin, NT-13317 was administered orally at the dose of 100 mg/kg, for 3 weeks, (5 times/week, Monday through Friday). Such administration schedule produced an anti pain effect that was maximal at the end of week 3. Moreover, after the last dosing there was still a beneficial effect at 4 h, a time much longer than the molecule half life.

Furthermore, the effects of NT-11624 were tested in a model of knee OA in rats. A single intraarticular injection of monosodium iodoacetate (MIA) in the rat knee joint induces an initial inflammatory response that subsides after 7 days leaving a cartilage damage similar to late stage human OA. Rats show painful neuropathic condition revealed by abnormal posture with the body weight charged on the healthy side, as well as hyperalgesic (excessive pain perception) and allodynic (painful perception of other sensory stimuli, i.e. tactile, pressure, thermal etc) responses. After 2 weeks of oral administration of 75 and 150 mg/kg b.i.d. of NT-11624 the paw pressure hyperalgesic response was tested. Surprisingly, already at the pre last administration test (13 h after the evening administration of the previous day, both treated groups demonstrated a significant reduction of the hyperalgesia. Six further testing session were performed starting 15 min until 48 h after last dosing. NT-11624 at 150 mg/kg produced an anti-hyperalgesic effect that lasted throughout the experiment. These data show that after a 2 week treatment there is a carry over effect and that NT-11624 produces a beneficial effect that lasts for at least 48 h.

Example 1 ddC Induced Peripheral Neuropathic Pain

Painful peripheral NP may be induced in rats by i.v. administration of 2',3'-dideoxycytidine (ddC) mimicking what is seen in AIDS patients undergoing antiviral therapy. The ddC test represents a useful and predictive model to study molecules with analgesic potential in human neuropathic states.

This study aimed at confirming that both an enhanced and a prolonged anti pain effect result from chronic NT-11624 administration. For said purpose, two different administration schedules of NT-11624 were given to rats in which a painful neuropathy had been induced by administration of ddC and compared to the effects of a stable dose schedule for an equal period of time of pregabalin, used as standard reference.

Adult male SD rats (Harlan, Italy, 150-200 g weight) were used. Animals were treated with 25 mg/kg i.v. bolus of 2',3'-dideoxycytidine, an inhibitor of nucleoside reverse transcriptase used for AIDS therapy that in rodents induces a peripheral neuropathy resulting in allodynic responses to mechanical stimuli. Symptoms severity peaks between 5 to 10 days after administration (Joseph, E. K. et al. —Pain 107 (2004) 147-158). Ten days after administration of ddC, as an intravenous (i.v.) bolus, test substances were administered every day, once a day or b.i.d for 4 weeks. Dosing was withheld in those days in which allodynic tests were performed, and lasted for 24 h and 48 h.

NT-11624 was dissolved in distilled water and was orally by gavage administered as follows Group 1: 100 mg/kg b.i.d. for 14 days, followed by 50 mg/kg b.i.d. for 7 days, then 50 mg/kg u.i.d. for 7 days.
Group 2: 50 mg/kg b.i.d. for 28 days.

Pregabalin (3B Pharmachem (Wuhan) International Co.) was dissolved in 1% CMC (carboxymethylcellulose) and orally administered at the dose of 15 mg/kg b.i.d. for 28 days.

Thresholds for mechanical allodynia were measured using an electronic Von Frey apparatus. Allodynic responses were assessed at time 0 (pre-drug) and 60 min following drug administration at day 1, 3, 7, 10, 14, 21 and 28. After 4 week drug administration, additional tests were performed beyond the 60 min point, at 4, 8, 24, 48 and 56 h. Results represent the mean (±S.E.M.) of mechanical thresholds expressed in grams.

Figure 2:
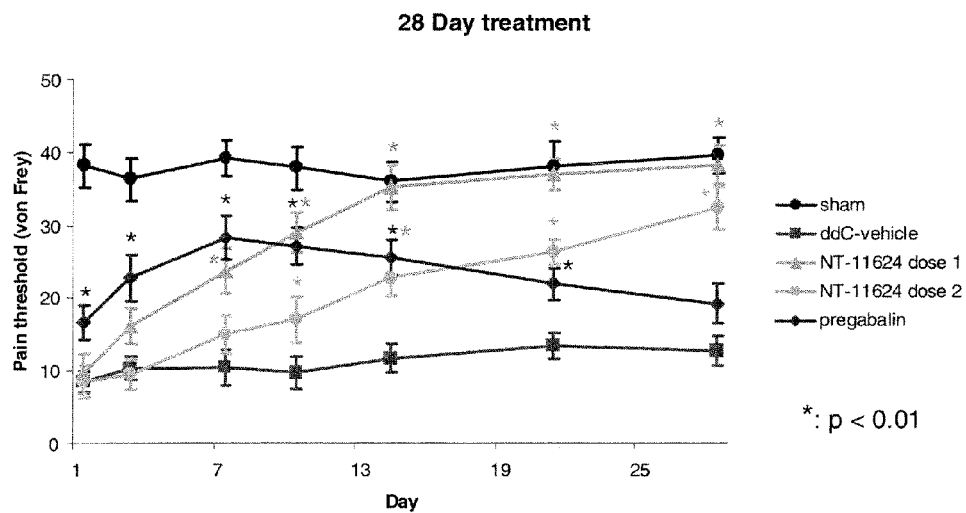
FIG. 2 shows the effect of NT-11624 and pregabalin after repeated (28 days) oral administration on mechanical allodynia induced in rats by ddC treatment. The von Frey test was performed at 1 h after administration. sham: saline, vehicle
Figure 3:
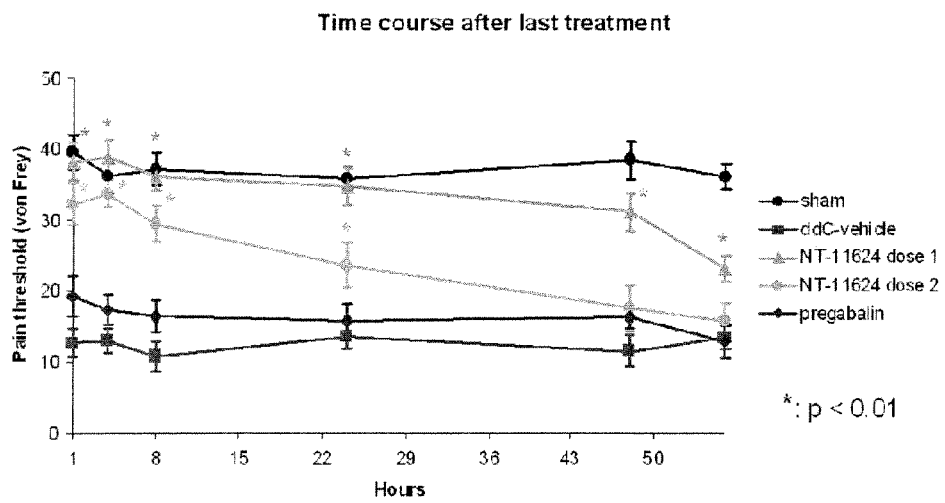
FIG. 3 shows the effect of NT-11624 and pregabalin after repeated (28 days) oral administration of ddC inducing mechanical allodynia in rats; the von Frey test was performed on day 28, at 1, 4, 8, 24, 48 and 56 h after administration, sham: saline, vehicle
Figure 4:
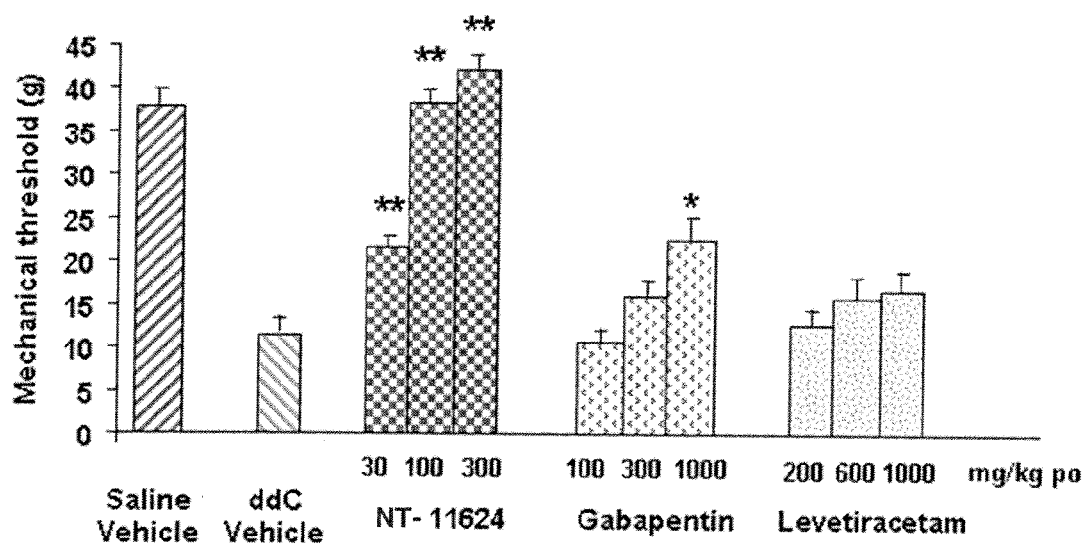
FIG. 4 shows that NT-11624, but not gabapentin or levetiracetam, fully reverts ddC-induced neuropathy in the rat. Each value represents the mean (±SD) of two experiments performed in the same experimental conditions. The mechanical threshold (von Frey) expressed as grams is referred at 15 min after drug administration. *$P<0.05$, **$P<0.01$ versus ddC-vehicle treated rats.

FIG. 2 reports the results obtained following repeated oral administration of NT-11624 with two different dose and treatment schedule groups and pregabalin on mechanical allodynia induced by ddC treatment in rat.

In group 1 (down-titration schedule), a significant anti-allodynic effect was displayed by NT-11624 starting from the third day after the first administration and increasing with time, reaching a complete protection at day 14. Thereafter, in spite of the dose halving for an entire week, the anti-pain effect was retained at its peak (full reversal of the threshold to the same level of non lesioned animals). In the last week of the experiment, a further dose reduction was done from 50 mg b.i.d. to 50 mg u.i.d. Repeated testing was performed until 56 h after last dosing. Very interestingly, up to 48 h from the last administration (at day 28), NT-11624 still produced a full reversal of allodynia. A still significant protection was also observed after 56 h from the last administration.

NT-11624 at a lowered but steady dose induced an incremental anti-pain response starting from day 10 until the end of the experiment. With this treatment schedule too, after the last NT-11624 administration there was a prolonged duration of effect clearly evident up to 24 h, waning, but being still significant at 48 h.

Pregabalin reached its peak effect a day 14, steadily declining in efficacy after that. The last administration on day 28 produced a moderate beneficial effect that disappeared after 8 h.

Von Frey test: The administration of ddC produced a remarkable diminution of the allodynic threshold at all test session. The threshold dropped down to about ¼ of the threshold found in healthy not treated controls.

Pregabalin 15 mg p.o. b.i.d. had a modest but significant effect already from day 1; this increased up to day 7, and then plateaued until day 14, to decline thereafter.

NT-11624 at the steady oral dose of 50 mg b.i.d. became efficacious as of day 10, steadily increasing afterwards until day 28. After the last dosing the beneficial effect was still evident at 48 h.

NT-11624 administered 100 mg/kg b.i.d. for 14 days, and then 50 mg/kg b.i.d. for 7 days, then 50 mg/kg u.i.d. for the last 7 days, started relieving allodynia as of day 3. Then, in spite of the reduced dose it became progressively more effective and from day 14 until the end of the experiment brought the threshold back to the same level of the normal value as seen in, non ddC treated animals. It is noteworthy that even when the dose was spaced from b.i.d. to once a day (u.i.d.) there was no decrease in efficacy. After last dosing, a full reversal of allodynia was seen up to 48 h and a robust effect was seen even at 56 h.

Conclusions:

This study demonstrated that:

1. NT-11624 is an effective compound to treat neuropathic pain induced by systemic ddC.

2. Once appeared, the anti allodynic effect of NT-11624 does not show tolerance but on the contrary increases progressively. The level of improvement is maintained even when the dose has been halved and the timing of dosing spaced and/or reduced;

3. Upon chronic treatment, NT-11624 showed a very prolonged effect that outlasts several half lives of the molecule in the body.

In conclusion, this study demonstrates that chronic treatment with an acetam derivative produces incremental therapeutic effect which are maintained on chronic treatment in spite of dose reduction and more distantly spaced dose administrations Materials and Methods Animals: Adult male SD rats (Harlan, Italy 150-200 g weight at arrival), were used. The animals were single housed in polypropylene cage until time of surgery. Room temperature and relative humidity were constantly kept at 22±2° C. and 55±15%, respectively, and a 12 hour light and 12 hour darkness cycles maintained. Food and water were freely available.

Drugs: The following substance was used: NT-11624 (batch No. 0000104580 supplied by Brane Discovery Srl, Gerenzano Italy). NT-11624 was dissolved in distilled water and given p.o. every day, except in those days in which allodynic tests were performed and lasted for 24 h, 48 h and 56 h (i.e. days 1, 3, 7, 10, 14, 21, 28).

The following groups of treatment were utilized:

NT-11624 (Group 1): rats received 100 mg/kg b.i.d. of NT-11624 for 14 days, then 50 mg/kg b.i.d. for 7 days, then 50 mg/kg u.i.d. for 7 days.

NT-11624 (Group 2): rats received 50 mg/kg b.i.d. for 28 days

Pregabalin: rats received 15 mg/kg b.i.d. for 28 days

Administration volume was 10 ml/kg body weight. Pregabalin [3B Pharmachem (Wuhan), International Co] was dissolved in CMC 1% (carboxymethylcellulose, Sigma-Aldrich, Italy), and orally given as described before. Control rats received vehicle only.

ddC intravenous injection: ddC was dissolved in saline to a concentration of 25 mg/kg (1 ml) and was administered i.v. into the rat tail vein. Control rats were treated with an equal volume of saline i.v.

The administration of ddC produces dose-dependent mechanical hypersensitivity and allodynia peaking in severity between 5-10 days after the administration. The test is usually performed at day 10.

Von Frey test: Each animal was placed in a chamber with a mesh metal floor covered by a plastic dome that enabled the animal to walk freely, but not to jump. The mechanical stimulus was then delivered in the mid-plantar skin of left hind paw using an electronic Von Frey apparatus (37400 Dynamic Plantar Aesthesiometer; Ugo Basile, Comerio, Varese, Italy). The cut-off was fixed at 50 g, while the increasing force rate (ramp duration) was settled at 20 sec. The mechanical allodynia thresholds were measured before (pre-test) and 60 min following drug administration at day 1, 3, 7, 10, 14, 21, 28. At day 28, additional tests were performed at 4, 8, 24, 48 and 56 h after drug administration. Results represent the mean (±S.E.M.) of mechanical thresholds expressed as grams.

Statistical analysis: All experimental results are given as the mean±S.E.M. An analysis of variance, ANOVA, followed by Fisher's protected least significant difference procedure for post hoc comparison, were used to verify significance between two means of behavioural results. Data were analyzed with the StatView software for the Macintosh (1992). P values≤0.05 were considered significant.

Data of mechanical threshold (PWT) were converted to a percentage of the maximal possible effect (% MPE), according to (Veneroni, O. et al. —Pain 102 (2003) 17-25), with slight modification, as follows:

$$\%MPE = (\text{left post-dose } PWT - \text{left pre-dose Control } PWT)/(\text{left naïve } PWT - \text{left pre-dose } PWT)*100$$

Control is the ddC-vehicle treated group.

Example 2

Monoiodo Acetic Acid (MIA)-Induced Osteoarthritis Pain: Effect of NT-11624

Peripheral neuropathic induced in rats by administration into the left knee joint of MIA mimics chronic pain condition of osteoarthritis found in a large part of population over 60 years. The MIA test represents an useful and predictive model to study the anti-hyperalgesic potential of a drug in human osteoarthritic condition.

Aim of this study was to evaluate the effect of repeated oral administration of NT-11624 (i.e. dimiracetam) and tramadol on mechanical hyperalgesia in rats in the MIA model.

Materials and Methods

Animals: Adult male SD rats (Harlan, Italy 150-200 g weight at arrival), were used. Four rats were housed per cage and fed a standard laboratory diet. Food and water were freely available. Room temperature and relative humidity were constantly kept at 22±2° C. and 55±15%, respectively, and a 12 hour light and 12 hour darkness cycles maintained.

The experiments were carried out in accordance with the Animal Protection Law of the Republic of Italy, DL No. 116/1992, based on the European Communities Council Directive of 24 Nov. 1986 (86/609/EEC). All efforts were made to minimise animal suffering and to reduce the number of animals involved. The cages were brought into the experimental room the day before the experiment, for acclimatization purposes. All experiments were performed between 10:00 and 17:00.

Drugs: The following substances were used: NT-11624 (batch n 66-MM3/16 supplied by Brane Discovery Sri, Gerenzano Italy) and tramadol (Tocris, UK). NT-11624 (150 mg/kg) and tramadol (40 mg/kg) were dissolved in distilled water and orally given in a volume of 10 ml/kg body weight. Control rats received saline only.

Sodium monoiodoacetate injection: A single intra-articular injection of sodium iodoacetate (MIA) was introduced into the right knee joint. This treatment inhibits chondrocyte metabolism leading to cartilage degradation consistent with late stage osteoarthritis. Briefly, rats were deeply anaesthetized by ethylic ether. Following abolition of the hindpaw pinch withdrawal reflex, a 27-gauge needle was introduced into the joint cavity between the tibial plateau and femoral condyles. Once in place, 2 mg of MIA were solubilized in a volume of 25 ul and injected into the joint and the animal was allowed to recover for 14 days prior to pain assessment. It has consistently been shown that this dose of MIA causes osteoarthritic-like focal lesions in articular cartilage and subchondral bone thickening 14 days after administration Guingamp C. et al. Arthritis Rheum 40, 1670-9 (1997). Therefore this model can easily and quickly reproduce osteoarthritic-like lesions and functional impairment in rats, similar to that observed in human disease.

The administration of MIA induces in rats a hyperalgesic response to mechanical stimuli that reaches its statistical significance 5 days after administration and persists for 4 weeks (Fernihough et al. Pain 112:83-93 (2004)).

Control rats were treated with an equal volume of saline. Animals received a repeated administration (14 days b.i.d.) of NT-11624 (150 mg/kg p.o.) or tramadol (40 mg/kg p.o.), or saline starting 3 days after MIA injection.

Starting from day 17 after MIA injection, paw pressure tests were performed.

Mechanical hyperalgesia: Paw mechanical sensitivity was determined using a Randall & Selitto apparatus exerting a force that increases at constant rate (32 g/s). The stimulus at which rats withdrawn the paw was evaluated before treatment (First day basal) and at the end of the treatment as following: before last treatment (pre-dose), and after last treatment (15, 30, 45, 60 min, 24, 48 and 72 h).

Results represent the mean of mechanical thresholds expressed as grams. To avoid any possible damage to the animal paw the maximum applied force was fixed at 240 g.

Results

Table 1 reports the results obtained after acute and repeated oral administration of NT-11624 and tramadol at the dose of 150 mg/kg and 40 mg/kg respectively. NT-11624 (treatment for 14 days, b.i.d.) completely protects from MIA-induced hyperalgesia up to 24 h after the last injection, with a statistically significant activity also at 48 h. In the same experimental conditions tramadol (treatment for 14 days, b.i.d.) exerts only a weak antihyperalgesic activity 15 and 30 min after the last treatment. In the same experiment, two groups of rats were treated with saline b.i.d. for 14 days; after this, a single oral dose of NT-11624 (150 mg/kg) or tramadol (40 mg/kg) was administered and mechanical threshold was measured. NT-11624 produced a significant increase of mechanical threshold only at 30 min after the administration, while tramadol caused a significant anti-hyperalgesic effect from 15 to 60 min; data are in agreement with those obtained in the previous acute experiment and demonstrate that chronic treatment with NT-11624 improves antihyperalgesic effects in this model.

Conclusions:

NT-11624 exhibits a complete reduction of rat hyperalgesia induced by monosodium iodoacetate injected into the knee joint; it therefore represents a potential therapeutic compound for the relief of neuropathies induced by osteoarthritis, an area of high therapeutic interest.

TABLE 1

EFFECT OF NT-11624 REPEATED ADMINISTRATION ON MIA
INDUCED HYPERALGESIA IN THE RAT (PAW-PRESSURE TEST)

| TREATMENT mg/kg p.o. | Mechanical threshold(g) | | | | |
|---|---|---|---|---|---|
| | Before Treatment First day | Before last treatment | After last treatment | | |
| 14 days b.i.d. | basal | pre-dose | 15 min | 30 min | 45 min |
| SALINE + vehicle | 51.9 ± 2.8 | 64.6 ± 3.6 | 63.4 ± 4.2 | 65.3 ± 4.2 | 65.8 ± 3.9 |
| MIA + vehicle | 61.0 ± 2.9 | 25.6 ± 3.1 | 22.5 ± 3.7 | 26.2 ± 3.9 | 24.9 ± 4.6 |
| MIA + NT-11624 150 | 63.5 ± 3.2 | 65.1 ± 2.5** | 72.6 ± 4.1** | 75.0 ± 2.2** | 70.5 ± 2.7** |
| MIA + TRAMADOL 40 | 59.2 ± 3.1 | 33.4 ± 2..9 | 38.8 ± 2.2* | 36.4 ± 2.9* | 32.8 ± 3.4 |
| MIA + vehicle (Single administration on saline 14 days b.i.d.) | 58.9 ± 3.0 | 24.7 ± 4.5 | 21.9 ± 3.8 | 25.3 ± 4.6 | 27.6 ± 3.7 |
| MIA + NT-11624 150 (Single administration on saline b.i.d.) | 60.4 ± 2.7 | 23.9 ± 3.5 | 33.8 ± 3.1 | 39.3 ± 2.8* | 26.2 ± 3.1 |
| MIA + TRAMADOL 40 (Single administration on saline b.i.d.) | 62.8 ± 3.0 | 25.5 ± 3.8 | 39.2 ± 4.1* | 43.4 ± 3.6** | 36.2 ± 3.4* |

| TREATMENT mg/kg p.o. | Mechanical threshold(g) After last treatment | | | |
|---|---|---|---|---|
| 14 days b.i.d. | 60 min | 24 h | 48 h | 72 h |
| SALINE + vehicle | 60.9 ± 4.3 | 61.8 ± 2.5 | 64.1 ± 4.4 | 61.3 ± 4.0§ |
| MIA + vehicle | 22.3 ± 3.9 | 24.7 ± 3.8 | 25.8 ± 3.0 | 23.5 ± 3.5§ |
| MIA + NT-11624 150 | 60.6 ± 4.2** | 55.3 ± 4.8** | 43.9 ± 4.0** | 34.8 ± 3.7§ |
| MIA + TRAMADOL 40 | N.D. | N.D. | N.D. | N.D. |
| MIA + vehicle (Single administration on saline 14 days b.i.d.) | 24.1 ± 4.8 | N.D. | N.D. | N.D. |
| MIA + NT-11624 150 (Single administration on saline b.i.d.) | N.D. | N.D. | N.D. | N.D. |
| MIA + TRAMADOL 40 (Single administration on saline b.i.d.) | 27.2 ± 3.4 | N.D. | N.D. | N.D. |

MIA (sodium monoiodoacetate) 2 mg in a volume of 25 µl was injected into the left knee joint of anaesthetised rats.
Each value represents the mean of 8 rats (2 exp.).
§ values are the mean of 4 rats.
Paw pressure test was performed before treatment (First day basal) and at the end of the treatment as following: before last treatment (pre-dose), and after last treatment (15, 30, 45, 60 min, 24, 48 and 72 h).
*$p < 0.05$,
**$p < 0.01$ versus MIA-vehicle treated rats.
Results represent the mean ± S.E.M. of mechanical thresholds expressed as grams.
N.D.: not determined

Example 3

Oxaliplatin-Induced Peripheral Neuropathy: Effect of Chronic NT-13317

Treatment with chemotherapy drugs frequently causes the development of peripheral neuropathy consisting of mechanical and cold allodynia, ongoing burning pain, tingling and numbness. There is currently no effective treatment to prevent or reverse chemotherapy-induced neuropathy.

Materials and Methods

Animals: Adult male SD rats (Harlan, Italy 150-200 g weight at arrival), were used. Four rats were housed per cage and fed a standard laboratory diet. Food and water were freely available. Room temperature and relative humidity were constantly kept at 22±2° C. and 55±15%, respectively, and a 12 hour light and 12 hour darkness cycles maintained.

The experiments were carried out in accordance with the Animal Protection Law of the Republic of Italy, DL No. 116/1992, based on the European Communities Council Directive of 24 Nov. 1986 (86/609/EEC). All efforts were made to minimise animal suffering and to reduce the number of animals involved. The cages were brought into the experimental room the day before the experiment, for acclimatization purposes. All experiments were performed between 10:00 and 17:00.

Drugs: The following substance was used: NT-13317 (batch No. RR0011-184A1 supplied by Brane Discovery Srl, Gerenzano Italy). NT-13317 was dissolved in DMSO 20%, 10% glucose and administered at the dose of 10, 30 and 100 mg/kg p.o.

Gabapentin (Sigma) was dissolved in 1% CMC (carboxymethylcellulose-Sigma) and orally administered at 100 mg/kg, and dissolved in saline and i.v. administered at 3 mg/kg.

Oxaliplatin model: A peripheral neuropathy was induced in adult rats, by administration of oxaliplatin (Tocris), at 2.4 mg/kg i.p. in saline once a day on days 1, 2, 3, 4, 5, 8, 9, 10, 11, 12, 15, 16, 17, 18, 19 (cumulative dose 36 mg/kg) according to [1].

In the first experiment NT-13317 and gabapentin were given chronically at the dose 100 mg/kg po starting 3 days before oxaliplatin and every day for 5 days/week for 3 weeks.

A dose-response experiment was then performed with NT-13317 (10, 30 and 100 mg/kg po) using the same treatment schedule.

Paw pressure test: Paw mechanical sensitivity was determined using a Randall & Selitto apparatus exerting a force that increases at constant rate (32 g/s). The stimulus at which rats withdrawn the paw was evaluated before and at different times after treatment. Results represent the mean of mechanical thresholds expressed as grams. To avoid any possible damage to the animal paw the maximum applied force was fixed at 240 g.

Statistical analysis: All experimental results are given as the mean±S.E.M. An analysis of variance, ANOVA, followed by Fisher's protected least significant difference procedure for post hoc comparison, were used to verify significance between two means of behavioral results. Data were analyzed with the StatView software for the Macintosh (1992). P values≤0.05 were considered significant.

Results

NT-13317 administered once daily (100 mg/kg, po) from three days before oxaliplatin treatment, and continuing on the same days of oxaliplatin treatment produced a statistically significant reduction of mechanical hyperalgesia, which is evident after the first week of treatment and is maximal after three weeks of treatment (Table 1), Gabapentin in the same conditions was showing a much lower effect only at the end of the third week.

In a dose-response experiment NT-13317 was administered at 10, 30 and 100 mg/kg p.o. NT-13317 at 100 mg/kg confirmed the results of the first experiment, while the lower doses were inactive.

In both experiments an evaluation of the pharmacodynamic profile of NT-13317 and gabapentin was performed at the end of the third week. NT-13317 (100 mg/kg po) retained maximal efficacy up to 4 hr after its administration, while at 8 hr its effect was not any more significant (Table 1 and Table 2). Gabapentin only showed a sporadic, intermediate efficacy at 30 min after its administration, then rapidly decreasing to the vehicle level (Table 1).

Conclusions

NT-13317 has demonstrated a broad spectrum of antihyperalgesic activity against antitumor agents induced neuropathies. NT-13317 appears superior to the tested reference compounds. On chronic treatment schedule, NT-13317 did not show tolerance displaying, on the contrary, a prolonged effect.

Example 4

Chronic Constriction Injury of Sciatic Nerve in Rats: Effect of NT-13317

Aim of this study was to evaluate the effect of single and repeated administration of NT-13317 in comparison with Gabapentin on mechanical hyperalgesia and allodynia in the rat chronic constriction injury model.

Materials and Methods

Animals: Adult male SD rats (Harlan, Italy 150-200 g weight at arrival), were used. Four rats were housed per cage and fed a standard laboratory diet. Food and water were freely available. Room temperature and relative humidity were constantly kept at 22±2° C. and 55±15%, respectively, and a 12 hour light and 12 hour darkness cycles maintained.

The experiments were carried out in accordance with the Animal Protection Law of the Republic of Italy, DL No. 116/1992, based on the European Communities Council Directive of 24 Nov. 1986 (86/609/EEC). All efforts were made to minimise animal suffering and to reduce the number of animals involved. The cages were brought into the experimental room the day before the experiment, for acclimatization purposes. All experiments were performed between 10:00 and 17:00.

Drugs: The following substance was used: NT-13317 (batch n RR0011-184A1) supplied by Brane Discovery Sri, Gerenzano Italy).

In the repeated administration protocol, NT-13317 was orally administered at 100 mg/kg in 1% CMC once a day for 14 days starting from the day of sciatic nerve ligation.

Peripheral rat mononeuropathy (Chronic constriction injury): Neuropathy was induced according to the procedure described by Bennett and Xie (Bennett G J, Xie Y K. A peripheral mononeuropathy in rat that produces disorders of pain sensation like those seen in man. Pain 1988; 33: 87-107).

Briefly, rats were anaesthetized with chloral hydrate 400 mg/kg intraperitoneally (i.p.); under aseptic conditions, the right common sciatic nerve was exposed at the level of the middle thigh by blunt dissection. Proximal to the trifurcation, the nerve was carefully freed from the surrounding connective tissue and four chromic cat gut ligatures (4-0, Ethicon, Norderstedt, Germany) were tied loosely around it with about 1 mm spacing. After haemostasis was confirmed, the incision was closed in layers. Then animals were allowed to recover

TABLE 2

EFFECT OF NT-13317 AND GABAPENTIN ON OXALIPLATIN INDUCED HYPERALGESIA IN THE RAT PAW-PRESSURE TEST
Paw pressure in rats (g)
Time (weeks of oxaliplatin treatment)

| Treatment i.p. | Treatment p.o.. | Pre-test before all treatments | $1^a$ week - 30 min | $2^a$ week - 30 min | $3^a$ week - 30 min | $3^a$ week - 4 h | $3^a$ week - 8 h | $3^a$ week - 24 h |
|---|---|---|---|---|---|---|---|---|
| VEHICLE 1 | VEHICLE | 60.6 ± 3.8 | 64.5 ± 4.2 | 68.9 ± 5.7 | 77.3 ± 4.6 | 73.2 ± 4.2 | 71.0 ± 4.3 | 66.8 ± 3.1 |
| OXALIPLATIN | VEHICLE | 61.9 ± 4.2 | 50.7 ± 5.1 | 41.9 ± 5.1 | 42.2 ± 4.8 | 43.7 ± 3.8 | 41.5 ± 3.2 | 43.1 ± 4.0 |
| VEHICLE | NT-13317 100 | 60.6 ± 3.9 | 63.0 ± 4.3 | 66.1 ± 4.5 | 74.8 ± 5.4 | 73.8 ± 4.4 | 68.5 ± 3.7 | 69.9 ± 4.6 |
| OXALIPLATIN | NT-13317 100 | 58.9 ± 3.7 | 68.7 ± 5.2 | 74.3 ± 6.1* | 79.2 ± 6.3* | 74.3 ± 4.3* | 53.5 ± 6.3 | 40.6 ± 5.0 |
| VEHICLE | GABAPENTIN | 62.7 ± 3.9 | 65.6 ± 4.9 | 73.7 ± 5.2 | 82.3 ± 5.2 | 76.2 ± 4.8 | 78.2 ± 5.6 | 68.7 ± 5.9 |
| OXALIPLATIN | GABAPENTIN | 61.1 ± 4.0 | 47.8 ± 5.6 | 49.0 ± 5.5 | 59.5 ± 5.5* | 55.6 ± 4.2 | 43.8 ± 6.1 | 42.2 ± 5.5 |

Treatment: Oxaliplatin 2.4 mg kg$^{-1}$ for 5 consecutive days every week (15 i.p. injection -cumulative dose 36 mg/kg) Test which was performed 48 h after the last oxaliplatin injection. All drugs were administered once daily starting three days before oxaliplatin treatment and in the same days of chemotherapic injection. NT-13317 and gabapentin were administered 30 min, 4, 8 and 24 h before test determination. N = 11 rats per group (two experiments).
*P < 0.01 vs oxaliplatin-treated rats from anaesthesia and surgery and were kept one per cage with free access to water and standard laboratory chow.

Statistical analysis: All experimental results are given as the mean±S.E.M. An analysis of variance, ANOVA, followed by Fisher's protected least significant difference procedure for post hoc comparison, were used to verify significance between two means of behavioural results. Data were analyzed with the StatView software for the Macintosh (1992). P values≤0.05 were considered significant.

by i.c.v. single administration. NT-13317 was also active in the repeated administration model, so representing a potential therapeutic compound for the relief of neuropathies.

While there are shown and described presently preferred embodiments of the invention, it is to be distinctly understood that the invention is not limited thereto but may be otherwise variously embodied and practiced within the scope of the following claims.

TABLE 3

EFFECT OF BND 13317 (REPEATED TREATMENT) AND GABAPENTIN ON CHRONIC CONSTRICTION INJURY INDUCED HYPERALGESIA IN THE RAT (PAW-PRESSURE TEST)

| | | Paw pressure in rats (g) | | | |
| | | | Time | | |
| Treatment | Treatment p.o. | Pre-testbefore all treatments | 5 day 30 min | 10 day 30 min | 14 day 30 min |
| SHAM | VEHICLE | 58.3 ± 3.5 | 62.1 ± 4.4 | 57.9 ± 4.1 | 61.9 ± 4.9 |
| CCI | VEHICLE | 61.4 ± 2.9 | 39.7 ± 5.2 | 37.3 ± 5.5 | 33.7 ± 4.7 |
| SHAM | BND-13317 100 | 62.3 ± 3.5 | 57.7 ± 4.3 | 55.8 ± 5.0 | 59.2 ± 3.9 |
| CCI | BND-13317 100 | 60.7 ± 2.7 | 41.6 ± 4.2 | 51.9 ± 5.2** | 53.4 ± 5.5** |
| SHAM | GABAPENTIN 100 | 61.8 ± 2.9 | 63.2 ± 4.1 | 69.2 ± 5.1 | 71.2 ± 6.3 |
| CCI | GABAPENTIN 100 | 62.9 ± 3.3 | 52.4 ± 4.6** | 52.7 ± 5.6** | 56.7 ± 6.2** |

| | | Paw pressure in rats (g) | | | |
| | | | Time | | |
| Treatment | Treatment p.o. | 14 day 4 h | 14 day 8 h | 15 day 24 h | 18 day 3 days |
| SHAM | VEHICLE | 59.9 ± 4.1 | 62.5 ± 5.3 | 58.7 ± 4.3 | 64.2 ± 5.0 |
| CCI | VEHICLE | 36.6 ± 3.8 | 37.2 ± 5.1 | 35.9 ± 5.3 | 37.6 ± 4.6 |
| SHAM | BND-13317 100 | 57.2 ± 4.4 | 63.2 ± 6.0 | 61.6 ± 5.2 | 60.7 ± 6.2 |
| CCI | BND-13317 100 | 52.9 ± 5.2** | 51.6 ± 4.4** | 47.8 ± 4.7** | 43.6 ± 5.1 |
| SHAM | GABAPENTIN 100 | 69.2 ± 5.6 | 70.4 ± 5.9 | 68.5 ± 5.8 | 66.4 ± 4.8 |
| CCI | GABAPENTIN 100 | 57.1 ± 5.5** | 62.3 ± 6.5** | 59.6 ± 5.7** | 58.2 ± 5.5** |

Chronic constriction injury (CCI) is induced by sciatic nerve ligation; Each value represents the mean of 9-10 rats.
**P < 0.01;
*P < 0.05 versus CCI-vehicle treated rats; Results represent the mean ± S.E.M. of mechanical thresholds expressed as grams, n = 8 rats per group; END-13317 and gabapentin were administered once a day for 14 days starting from the day of sciatic nerve ligation.

Data of mechanical threshold (PWT) were converted to a percentage of the maximal possible effect (% MPE), according to Veneroni, O. et al. as follows:

$$\%MPE = (\text{left dose } PWT - \text{left pre-dose control } PWT)/(\text{left naïve } PWT - \text{left pre-dose } PWT)*100$$

The obtained % MPE were employed for $ED_{50}$ calculation (obtained by Grafit v. 5.0), defined as the dose producing 50% reversal of mechanical allodynia.

Results

Repeated Administration Protocol:

NT-13317 and gabapentin were administered p.o. at 100 mg/kg once a day for 14 days starting from the day of sciatic nerve ligation. In this conditions NT-13317 induced a significant effect on paw pressure test up to 24 hr after the last administration. Gabapentin was still active after 72 hr (Table 3).

Conclusions

NT-13317 exhibits a statistical significant reduction of rat hyperalgesia and allodynia induced by chronic constriction injury; NT-13317 was ten times more active than gabapentin

The invention claimed is:

1. A pharmaceutical administration form for monotherapy of neuropathic pain containing a plurality of dosage units consisting of dosage units for a first phase of treatment and dosage units for a second phase of the treatment, wherein
   each dosage unit for said first phase of treatment consists of an initial therapeutically effective dose of an acetam derivative in combination with one or more excipients
   and each dosage unit for said second phase of treatment consists of a subsequent dose of said acetam derivative in combination with one or more excipients,
   wherein the pharmaceutical administration form comprises dosage units for said first phase of treatment in at least 7 daily doses,
   wherein said dosage units for the first and the second phase of the treatment are physically separated,
   wherein the sum of the dosage units for a daily dose of said first phase contains at least 2 times the amount of the sum of the dosage units for a daily dose of said second phase, and
   said acetam derivative being selected from the group consisting of dimiracetam, (NT-11624), NT-13317, piracetam, aniracetam, oxiracetam, nefiracetam, levetiracetam, brivaracetam, seletracetam, rolziracetam, NT-15019, NT-24336, and NT-24337.

2. The pharmaceutical administration form of claim 1, comprising at least 14 dosage units for said first phase arranged for bi-daily administration.

3. The pharmaceutical administration form of claim 1, comprising 14 to 28 dosage units arranged for bi-daily administration.

4. The pharmaceutical administration form of claim 1, wherein the dosage units are arranged sequentially.

5. The pharmaceutical administration form of claim 4, being a blister pack.

6. The pharmaceutical administration form of claim 1, wherein the acetam derivative is selected from the group consisting of piracetam, oxiracetam, levetiracetam, and dimiracetam.

7. The pharmaceutical administration form of claim 6, wherein the acetam derivative is dimiracetam.

8. The pharmaceutical administration form of claim 4, being a blister pack and the acetam derivative being dimiracetam.

9. The pharmaceutical administration form of claim 1 wherein the acetam derivatives are selected from the group consisting of brivaracetam and seletracetam.

10. The pharmaceutical administration form of claim 1 wherein the acetam derivatives are selected form the group consisting of NT-13317 and NT-15019.

\* \* \* \* \*

UNITED STATES PATENT AND TRADEMARK OFFICE
CERTIFICATE OF CORRECTION

PATENT NO. : 9,125,898 B2
APPLICATION NO. : 12/566055
DATED : September 8, 2015
INVENTOR(S) : Carlo Farina et al.

Page 1 of 1

It is certified that error appears in the above-identified patent and that said Letters Patent is hereby corrected as shown below:

Title page

Item (75), "Valsoda" should be -- Valsolda --.

Signed and Sealed this
Thirty-first Day of May, 2016

Michelle K. Lee
*Director of the United States Patent and Trademark Office*